United States Patent
Jung et al.

(10) Patent No.: US 10,081,583 B2
(45) Date of Patent: Sep. 25, 2018

(54) STRIPPING METHOD

(71) Applicant: HANWHA CHEMICAL CORPORATION, Seoul (KR)

(72) Inventors: Ki Taeg Jung, Daejeon (KR); Hyo Suk Kim, Daejeon (KR); Young Jo Kim, Daejeon (KR); Kyong Jun Yoon, Daejeon (KR); Kee Do Han, Daejeon (KR)

(73) Assignee: HANWHA CHEMICAL CORPORATION, Seoul (KR)

(*) Notice: Subject to any disclaimer, the term of this patent is extended or adjusted under 35 U.S.C. 154(b) by 0 days.

(21) Appl. No.: 15/531,012

(22) PCT Filed: Dec. 7, 2015

(86) PCT No.: PCT/KR2015/013326
§ 371 (c)(1),
(2) Date: May 26, 2017

(87) PCT Pub. No.: WO2016/099062
PCT Pub. Date: Jun. 23, 2016

(65) Prior Publication Data
US 2017/0362148 A1    Dec. 21, 2017

(30) Foreign Application Priority Data

Dec. 18, 2014  (KR) .................. 10-2014-0183426
Dec. 4, 2015   (KR) .................. 10-2015-0172422

(51) Int. Cl.
C07C 29/74     (2006.01)
C07C 67/48     (2006.01)
(Continued)

(52) U.S. Cl.
CPC .............. *C07C 29/74* (2013.01); *C07C 29/80* (2013.01); *C07C 67/48* (2013.01); *C07C 67/54* (2013.01); *C07C 2601/14* (2017.05)

(58) Field of Classification Search
CPC ......... C07C 29/74; C07C 67/48; C07C 69/75; C07C 29/80; C07C 67/54; C07C 2601/14
See application file for complete search history.

(56) References Cited

U.S. PATENT DOCUMENTS 3,409,515 A * 11/1968 Baird .................. B01D 3/00
                                          159/16.1
7,893,295 B2 * 2/2011 Schlosberg .......... B01J 29/0308
                                          560/127
2006/0270868 A1  11/2006  Compton et al.

FOREIGN PATENT DOCUMENTS

CN      102060707        5/2011
KR   10-2003-0078919     10/2003
(Continued)

OTHER PUBLICATIONS

PCT Search Report & Written Opinion, Patent Cooperation Treaty, Application No. PCT/KR2015/013326, dated Jan. 21, 2016.
(Continued)

*Primary Examiner* — Pancham Bakshi
*Assistant Examiner* — Mark R Luderer
(74) *Attorney, Agent, or Firm* — Lex IP Meister, PLLC

(57) ABSTRACT

The present invention relates to a stripping method capable of recovering, by an environmentally friendly method, a high-purity ester-based compound without concern over the oxidation of an ester-based compound from a mixture containing the ester-based compound. The stripping method has advantages of generating no wastewater, enabling equipment costs to be reduced by simplifying the process, remov-
(Continued)

ing concern over the oxidation of an ester-based compound during the process, and enabling the reuse of the components recovered in the process.

8 Claims, 2 Drawing Sheets

(51) Int. Cl.
  *C07C 29/80* (2006.01)
  *C07C 67/54* (2006.01)

(56) References Cited

FOREIGN PATENT DOCUMENTS

| KR | 10-0495335 | | 6/2005 |
|---|---|---|---|
| KR | 10-2006-0118423 | | 11/2006 |
| KR | 10-2008-0017399 | | 2/2008 |
| WO | WO2013025277 | * | 2/2013 |

OTHER PUBLICATIONS

EPO, Extended European Search Report of the corresponding European Patent Application No. 15870229.0., dated Jul. 6, 2018.

* cited by examiner

[FIG. 1]
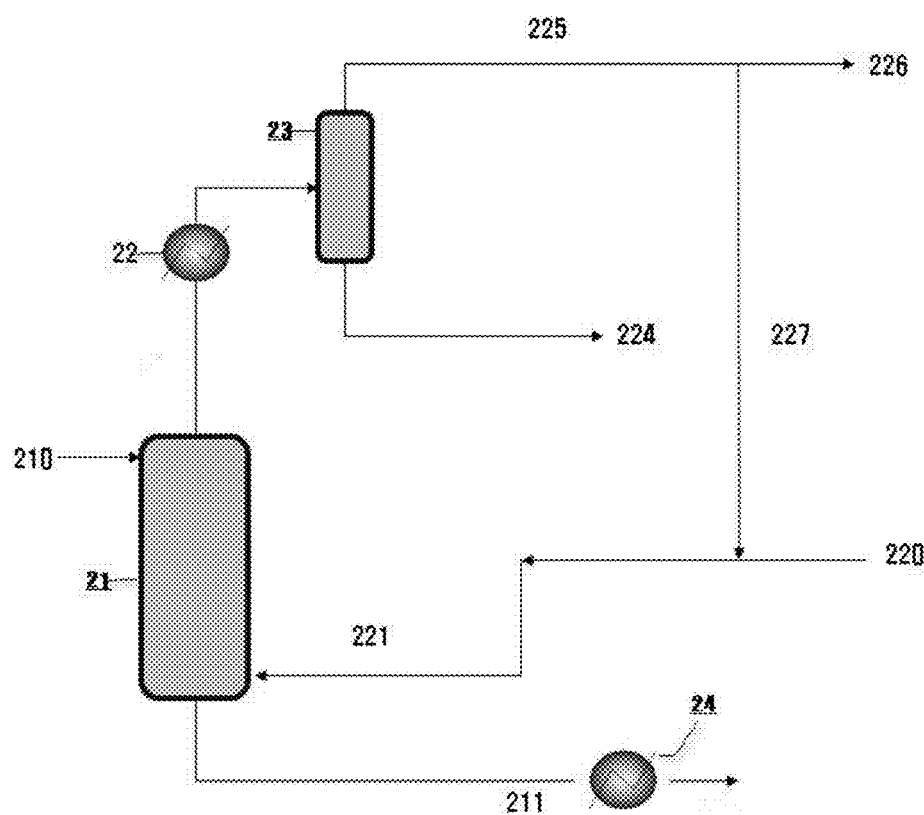

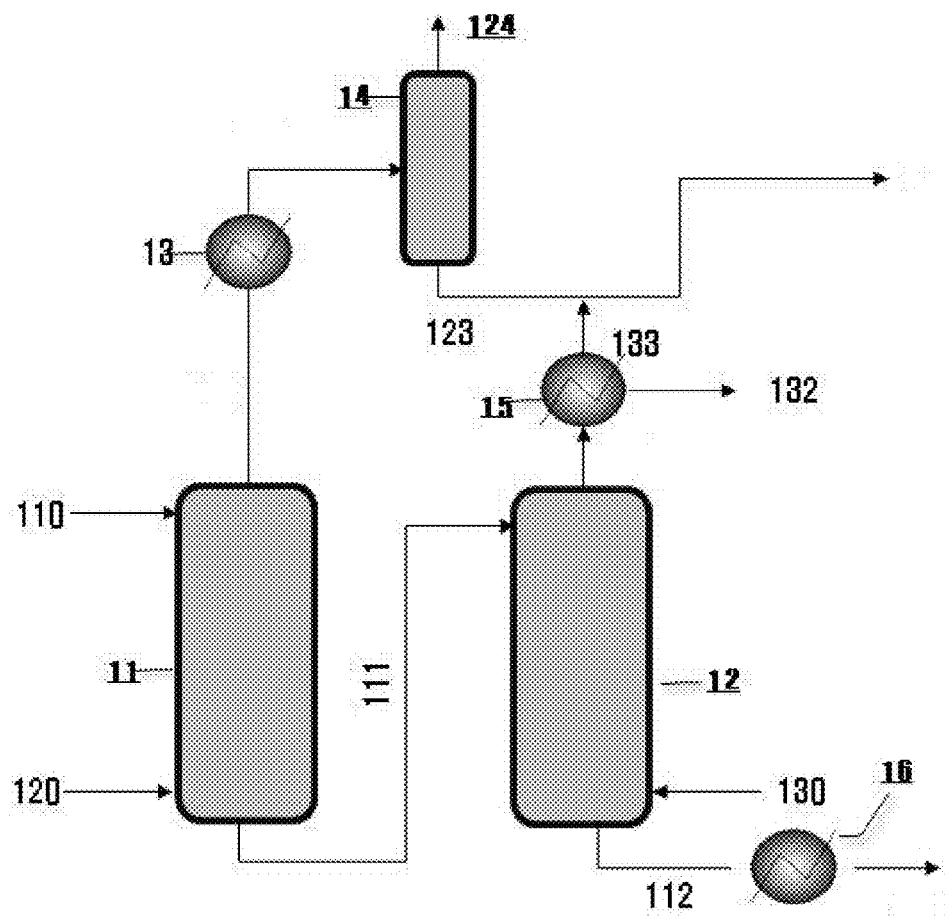
[FIG. 2]

STRIPPING METHOD

TECHNICAL FIELD

The present invention relates to a stripping method of an ester-based compound capable of recovering a high purity ester-based compound from a mixture including an ester-based compound in an environmentally-friendly manner.

BACKGROUND ART

An ester-based compound is a material used in various applications such as plastics, in particular, polyvinyl chloride plasticizers, electrical and electronic products, pharmaceuticals, paints, pigments, lubricants, binders, surfactants, adhesives, tile food containers, and packaging material, etc.

The ester-based compound is obtained as a mixture together with various by-products derived from a synthesis process or a commercialization process. When the ester-based compound in such a mixture state is commercialized, a desired effect may be deteriorated due to the by-products included in the mixture. In particular, when alcohol is included in the mixture of the ester-based compound, odor may occur in a final product, and thus, it is not capable of being practically used.

Thus, a steam stripping process in which the mixture including the ester-based compound is contacted with steam to remove alcohol from the mixture of the ester-based compound, was introduced. In the steam stripping process, the mixture of ester-based compound may be contacted with steam, and thus, alcohol from the mixture including the ester-based compound may be removed. However, according to the steam stripping method, a nitrogen stripping process in which the mixture from which alcohol is removed is contacted with nitrogen should be essentially included to remove condensed moisture due to steam in the mixture from which alcohol is removed. Therefore, when the steam stripping process is used, at least two or more processes have to be employed to purify the ester-based compound.

DISCLOSURE

Technical Problem

The conventional steam stripping process has problems in that a large amount of wastewater is caused by using steam, alcohol obtained from the steam stripping process is not able to be reused since it is obtained as a mixture with water, and an ester-based compound is oxidized by steam while the alcohol is removed from the mixture.

The present invention has been made in an effort to provide a stripping method having advantages of recovering a high purity ester-based compound without concern of oxidation from the mixture including the ester-based compound without causing wastewater in an environmentally-friendly manner, and reusing the alcohol recovered from the mixture.

Technical Solution

An exemplary embodiment of the present invention provides a stripping method including contacting a mixture including a cyclohexane dicarboxylic acid ester-based compound with an inert gas under a relative pressure of −1.0 to −0.5 barg to remove a volatile component from the mixture, thereby obtaining the cyclohexane dicarboxylic acid ester-based compound.

The mixture may include 1,000 ppm or more of alcohol.

The stripping method may further include supplying the volatile component recovered by contacting the mixture with the inert gas to a synthesis process or a subsequent treatment process of the ester-based compound. In addition, the stripping method may further include circulating the inert gas recovered after contacting the mixture with the inert gas, and then contacting the recovered inert gas with a new mixture.

The mixture may be contacted with the inert gas at a temperature ranging from 120 to 250° C. For example, the mixture may be heated to 120 to 250° C., the inert gas may be heated to 120 to 250° C., and then the heated mixture may be contacted with the heated inert gas, and thus, the mixture may be contacted with the inert gas in the above-described temperature range.

A weight ratio of the mixture and the inert gas may be 5 to 30:1.

Specifically, the stripping method may recover a high purity cyclohexane dicarboxylic acid ester-based compound from a reaction product obtained by hydrogenating a phthalate-based compound as a mixture. In addition, since the volatile component recovered from the reaction product includes a very small amount of moisture of 500 ppm or less, the volatile component may be reused in various processes. For example, the volatile component may be alcohol, and more specifically, 2-ethylhexanol.

Advantageous Effects

According to an exemplary embodiment of the present invention, there is provided a stripping method including: recovering a high purity ester-based compound from a mixture of a cyclohexane dicarboxylic acid ester-based compound using a simple method. The stripping method has advantages in that wastewater is not caused, equipment cost is able to be reduced by simplifying a process, the ester-based compound may not be oxidized in the process, and components recovered in the process are able to be reused.

DESCRIPTION OF THE DRAWINGS

FIG. 1 schematically shows a stripping device according to an exemplary embodiment.

FIG. 2 schematically shows a conventional stripping device.

MODE FOR INVENTION

Hereinafter, a stripping method according to a specific embodiment of the present invention is described below.

The stripping method is a method used to remove volatile components, etc., included in liquid. According to an exemplary embodiment of the present invention, there is provided a stripping method capable of being employed as a purification process or any one process of the purification process of an ester-based compound in order to recover the ester-based compound from a mixture including a cyclohexane dicarboxylic acid ester-based compound (hereinafter, referred to simply as 'an ester-based compound').

According to an exemplary embodiment of the present invention, the stripping method includes contacting a mixture including a cyclohexane dicarboxylic acid ester-based compound with an inert gas under a relative pressure of −1.0 to −0.5 barg (an absolute pressure of 0 to 0.5 bar) to remove a volatile component from the mixture, thereby obtaining the cyclohexane dicarboxylic acid ester-based compound.

The mixture may be a reaction product obtained by hydrogenating a phthalate-based compound. The mixture obtained by hydrogenating the phthalate-based compound may include various by-products derived from raw material or by-products, in addition to the ester-based compound. Among them, alcohol included in the mixture has a serious problem in commercializing the ester-based compound since it causes odor.

In order to solve the problem, in the conventional method, the alcohol is removed from the mixture including the ester-based compound by using a steam stripping process in which the mixture including the ester-based compound is contacted with steam. However, when the steam is used as described in the conventional method, a mixture including moisture in a condensed state is obtained. Accordingly, in order to remove the condensed moisture from the mixture from which alcohol is removed, the conventional method requires a nitrogen stripping process in which the mixture from which alcohol is removed is contacted with nitrogen, and thus, at least two or more processes have to be employed. In addition, the steam stripping process has problems in that a large amount of wastewater is caused by using steam, the alcohol obtained from the steam stripping process is not able to be reused since it is obtained as a mixture with water, and the ester-based compound is oxidized due to oxygen dissolved in the steam while the alcohol is removed from the mixture.

In order to solve the problems, the stripping method according to the exemplary embodiment employs special process conditions. Specifically, according to the stripping method of the exemplary embodiment, the mixture of the ester-based compound may be contacted with the inert gas to remove volatile components such as alcohol, etc., from the mixture, thereby recovering a high purity ester-based compound. More specifically, the stripping method may recover the high purity ester-based compound from the mixture by contacting the mixture including 1,000 ppm or more of alcohol with the inert gas. An upper limit of the alcohol content in the mixture is not particularly limited, but may be controlled to 300,000 ppm or less for effective stripping. According to the stripping method, since the steam is not used, wastewater is not caused, which is environmentally-friendly, and the volatile components such as alcohol, etc., may be recovered in a non-contaminated state, and thus, the recovered alcohol may be reused in a synthesis process or a subsequent treatment process of the ester-based compound.

The stripping method will be described in more detail with reference to FIG. 1.

A column may be used in the stripping method as shown in FIG. 1. Examples of the column may include a packing column, a tray column, or a spinning cone, etc., but is not limited thereto.

A mixture 210 including an ester-based compound may be supplied to an upper part of a column 21 and contacted with an inert gas 221 supplied to a lower part of the column 21, as shown in FIG. 1. When the mixture 210 is contacted with the inert gas 221, the volatile components such as alcohol, etc., contained in the mixture 210 may be discharged to the upper part of the column 21 together with the inert gas, and the ester-based compound 211 in which the volatile components are removed from the mixture 210 may be discharged to the lower part of the column 21.

The mixture 210 may be supplied to the upper part of the column 21 substantially in a liquid state even though it may vary depending on the kind of the ester-based compound included therein. The mixture 210 in a liquid state may be effectively stripped as an area in contact with the inert gas 221 is wider. Thus, the mixture may be sprayed in various types capable of producing droplets to maximize contact with the inert gas.

As the inert gas, various gases may be used as long as they do not react with the ester-based compound in the stripping process. As non-limiting examples, the inert gas may be helium, neon, argon, krypton, radon, xenon, nitrogen, carbon dioxide, freon or a mixture thereof. In addition, the inert gas may be a gas obtained by mixing at least one of the above-described gases with atmospheric air.

Since the mixture is contacted with the inert gas rather than steam, the ester-based compound in the mixture may not be oxidized. However, when process conditions become severe, the ester-based compound may be oxidized, etc., that is, may be damaged even though the inert gas is used. Thus, the mixture may be contacted with the inert gas under appropriate temperature and pressure.

For example, the mixture may be contacted with the inert gas at a temperature ranging from 120 to 250° C., from 120 to 200° C., or from 120 to 180° C. If the mixture is contacted with the inert gas at a temperature lower than the above-described range, a purification effect of the mixture may be deteriorated, and if the ester-based compound is contacted with the inert gas at a temperature higher than the above-described range, the ester-based compound may be oxidized or a product provided from the ester-based compound may have a problem in quality. At the time of using the column, temperatures of the stripping process may be different for each part of the column. Accordingly, when the column is used, the temperature of the lower part of the column may be controlled within the above-described range.

The stripping method may be performed under a negative pressure so that the mixture and the inert gas are able to be contacted with each other in the above-described temperature range. As an example, the mixture may be contacted with the inert gas under a relative pressure of −0.5 barg or less, −0.6 barg or less, or −0.7 barg or less. A lower limit of the pressure is not particularly limited, and for example, may be controlled to −1.0 barg or more.

As an example, according to the stripping method, the pressure of the column 21 may be controlled to the above-described range, and then, the heated mixture 210 may be supplied to the upper part of the column 21, and the heated inert gas 221 may be supplied to the lower part of the column 21, such that the mixture and the inert gas may be in contact with each other under the above-described temperature and pressure. Further, in order to maintain the temperature of the stripping process, a reboiler (not shown), etc., may be provided at the lower part of the column 21 to supply heat to the column. Here, the mixture may be heated to a temperature of, for example, 120 to 250° C., 120 to 200° C., or 150 to 200° C., and the inert gas may be heated to a temperature of, for example, 120 to 250° C., 120 to 200° C., or 120 to 180° C.

A weight ratio of the mixture and the inert gas may be controlled to be 5 to 30:1. If the used weight of the mixture is less than 5 times the weight of the inert gas, it is uneconomical since a large amount of energy is consumed to heat a large amount of inert gas and to cool the recovered ester-based compound. If the used weight of the mixture is more than 30 times the weight of the inert gas, the purification effect of the mixture may be deteriorated.

As shown in FIG. 1, when the mixture 210 is contacted with the inert gas 221, the volatile components of the mixture 210 may be discharged to the upper part of the column 21 together with the inert gas, and the high purity ester-based compound 211 obtained by removing the volatile components may be discharged to the lower part of the column 21.

The volatile components discharged together with the inert gas may be condensed through the condenser 22, and supplied to a drum 23. A liquid phase thereof may be discharged to a lower part of the drum 23, and a gas which is not condensed may be discharged to an upper part of the drum 23, and thus, the volatile components 224 such as alcohol, etc., and the inert gas 225 may be separated.

Since the above-obtained volatile components 224 such as alcohol, etc., are obtained in an uncontaminated state, the volatile components may be introduced into the synthesis process or the subsequent treatment process of the ester-based compound, and reused.

In addition, the inert gas 25 obtained as above may also be reused in the stripping process. As an example, a portion 226 of the inert gas 225 obtained as above may be purged, and other portion 227 thereof may be recovered and supplied back to the column 21 together with fresh inert gas 220. A recovered content of the inert gas 225 is not particularly limited, but for example, 50 to 99.9 wt % of the total inert gas may be recovered and reused.

A content of the volatile components remaining in the inert gas 225 may be controlled according to a level of an allowable residual amount of volatile components in a product to be produced by the ester-based compound 211 purified through the stripping process. In general, when a temperature of the condenser 2 is controlled to 40° C. or less, most of the volatile components in the inert gas may be condensed to separate the inert gas and the volatile components. If the allowable residual amount of the volatile components in the product to be produced by the ester-based compound 211 purified through the stripping process is 100 ppm or less, the temperature of the condenser 22 may be maintained lower than 40° C., and thus, the residual amount of the volatile components in the inert gas 227 to be reused may be further reduced. However, the temperature of the condenser 22 is not limited thereto, and may be appropriately controlled depending on the kind of the volatile components and the usage of the ester-based compound 211.

Meanwhile, the ester-based compound 211 obtained at the lower part of the column may be cooled through the cooler 24 and supplied to a storage tank or the subsequent process. The stream 211 obtained at the lower part of the column may include little alcohol, for example, may include alcohol at a level of 100 ppm or less or 50 ppm or less.

It may be understood that FIG. 1 schematically shows flow of the stripping process since power devices, etc., for preheating or transporting each stream are not separately shown in FIG. 1. Further, the stripping method may further include a process that is commonly employed in the technical field of the present invention.

Various compounds that are able to be used as a plasticizer may be exemplified as the ester-based compound that is able to be purified by the stripping method. Specifically, the ester-based compound may be a cyclohexane dicarboxylic acid ester compound, which has recently received attention as an environmentally-friendly plasticizer.

For example, a compound obtained by hydrogenating a phthalate-based compound to add hydrogen to a benzene ring of the phthalate-based compound, may be used as the cyclohexane dicarboxylic acid ester compound.

Examples of the phthalate-based compound may include dialkyl phthalate, diaryl phthalate, diaralkyl phthalate, alkylaryl phthalate, alkylaralkyl phthalate, arylaralkyl phthalate, dialkyl isophthalate, diaryl isophthalate, diaralkyl isophthalate, alkylaryl isophthalate, alkylaralkyl isophthalate, arylaralkyl isophthalate, dialkyl terephthalate, diaryl terephthalate, diaralkyl terephthalate, alkylaryl terephthalate, alkylaralkyl terephthalate, arylaralkyl terephthalate, or a mixture thereof, etc. Two substituents bonded to the phthalate-based compound may be the same as each other or different from each other. Specifically, the alkyl group may be a linear or branched alkyl group having 1 to 20 carbon atoms, 4 to 20 carbon atoms, or 5 to 10 carbon atoms, the aryl group may be an aryl group or a heteroaryl group having 6 to 30 carbon atoms, 6 to 20 carbon atoms, or 6 to 12 carbon atoms, and the aralkyl group may be an aralkyl group having 7 to 35 carbon atoms, 7 to 30 carbon atoms, or 7 to 25 carbon atoms. As a non-limiting example, the phthalate-based compound may include dibutyl phthalate (DBP), butyl benzyl phthalate (BBP), dihexyl phthalate (DHP), dioctyl phthalate (DOP), di-n-octyl phthalate (DnOP), diisononyl phthalate, diisodecyl phthalate (DIDP), dibutyl terephthalate (DBTP), dioctyl terephthalate (DOTP), diisononyl terephthalate (DINTP), diisodecyl terephthalate (DIDTP), dibutyl isophthalate (DBIP), dioctyl isophthalate (DOIP), diisononyl isophthalate (DINIP), diisodecyl isophthalate (DIDIP), or a mixture thereof. A method of hydrogenating the phthalate-based compound to obtain a corresponding cyclohexane dicarboxylic acid ester compound has already been disclosed, and thus a detailed description thereof will be omitted.

A high purity ester-based compound may be recovered from the mixture obtained by hydrogenating the phthalate-based compound using the above-described stripping method. In particular, when a reaction product obtained by hydrogenating a phthalate-based compound is contacted with the inert gas, high purity volatile components may be recovered from the reaction product. As an example, the volatile components recovered from the reaction product may include about 500 ppm or less of moisture. The recovered high purity volatile components may be reused in various processes. For example, the volatile component may be alcohol, and more specifically, 2-ethylhexanol.

The stripping method may remove the volatile components such as alcohol, etc., from the reaction product by a one-step process of contacting the reaction product with the inert gas, thereby recovering the high purity ester-based compound, and thus, it is possible to reduce equipment cost as compared to the conventional stripping method, and to secure process stability by a simple process.

Hereinafter, action and effects of the present invention are described by specific Examples of the present invention in detail. Meanwhile, these Examples are provided by way of example, and therefore, should not be construed as limiting the scope of the present invention.

Example 1

Diethylhexyl cyclohexanoate (DEHCH) was recovered from a mixture including 79 wt % of diethylhexyl cyclohexanoate (DEHCH), 20 wt % of 2-ethylhexanol, and 1 wt % of other impurities by using a device shown in FIG. 1.

As a column 21, a structure packing column in which an inner diameter is 100 mm, a height is 4 m, and an outside of the column is insulated with an insulating material was used.

The mixture 210 heated to about 180° C. was injected into an upper part of the column 21 at a flow rate of 30 kg/hr, and nitrogen 221 at about 140° C. was injected into a lower part of the column 21 at a flow rate of 3 kg/hr in a state that the column was operated by controlling an internal pressure of the column 21 to −0.8 barg (absolute pressure: 0.2 bar), wherein a weight ratio of the mixture and the inert gas was 10:1.

Temperatures of the mixture and nitrogen to be injected were controlled so that the temperature of the lower part of the column 21 was maintained at 145 to 155° C. during the operation of the column.

A stream obtained at the upper part of the column 21 was condensed through a condenser 22 and the condensed stream was accumulated in a drum 23. The drum 23 included condensed 2-ethylhexanol 224, and nitrogen 225 was discharged to an upper part of the drum 23 and a portion 227 thereof was reused, and the remainder 226 was purged. The condensed stream 211 obtained at the lower part of the column 21 was cooled through a cooler 24. It was confirmed that the cooled stream was diethylhexyl cyclohexanoate.

Example 2

Diethylhexyl cyclohexanoate was purified by stripping a mixture in the same manner as in Example 1, except that the internal pressure of the column was changed to −0.9 barg (absolute pressure: 0.1 bar).

Example 3

Diethylhexyl cyclohexanoate was purified by stripping a mixture in the same manner as in Example 1, except that the flow rate of nitrogen was changed to 1.5 kg/hr (a weight ratio of mixture and inert gas=20:1).

Comparative Example 1

Alcohol was removed from the same mixture as in Example 1 using a device shown in FIG. 2.

The same column 21 as Example 1 was used as two columns 11 and 12 in FIG. 2, and the internal pressure of the column 11 was controlled to −0.8 barg (absolute pressure: 0.2 bar).

The mixture 110 heated to about 180° C. was injected into an upper part of the column 11 at a flow rate of 30 kg/hr, and steam 120 heated to about 200° C. was injected into a lower part of the column at a flow rate of 7.5 kg/hr, wherein a weight ratio of the mixture and the steam was 4:1.

A temperature of the lower part of the column 11 was maintained at 145 to 155° C. during the operation of the column.

A stream obtained at the upper part of the column 11 was condensed through a condenser 13 and the condensed stream was accumulated in a decanter 14. The decanter 14 included 2-ethylhexanol 124 and a large amount of wastewater 123 derived from the steam.

A stream 111 obtained in the lower part of the column 11 was supplied to the upper part of the second column 12. Nitrogen heated to about 200° C. was injected into the lower part of the second column 12 at a flow rate of 3 kg/hr.

A temperature of the lower part of the column 12 was maintained at 140 to 150° C. during the operation of the second column 12.

The stream including wastewater and nitrogen was obtained at the upper part of the second column 12. The stream included 1.0 wt % of water, 1.0 wt % of alcohol, and the remaining contents of nitrogen. The stream was separated into the wastewater 133 and the nitrogen 132 through the condenser 15. The wastewater 133 was discharged together with the wastewater 123 discharged from the decanter 14.

In addition, diethylhexyl cyclohexanoate 112 was obtained at the lower part of the second column 12, and the diethylhexyl cyclohexanoate 112 was cooled through a cooler 16 and transported to a storage tank.

The alcohol 24 recovered from the decanter 14 included a large amount of moisture. Moisture is a factor that deteriorates performance of a catalyst used in a hydrogenation reaction process of a phthalate-based compound, and thus, alcohol including a large amount of moisture recovered from the decanter could not be reused in the hydrogenation reaction process of the phthalate-based compound. In addition, the wastewater 123 and 133 recovered in the decanter 14 and the condenser 15 could not be reused in other processes since they included a small amount of alcohol, and thus, it was confirmed that a large amount of alcohol and wastewater occurred when the method of Comparative Example 1 was used.

Comparative Example 2

Dioctyl terephthalate was purified by stripping a mixture in the same manner as in Comparative Example 1, except that nitrogen 132 discharged from the condenser 15 was supplied again to the second column 12.

Experimental Example

Used amounts of steam, nitrogen, cooling water, and chiller, etc., were shown in Table 1 below to compare energy efficiency, characteristics, etc., of the stripping processes of Examples 1 to 3 and Comparative Examples 1 and 2.

TABLE 1

| | Example 1 | Example 2 | Example 3 | Comparative Example 1 | Comparative Example 2 |
|---|---|---|---|---|---|
| Steam used amount [kg/hr] | 1.2 | 1.2 | 1.1 | 5.5 | 5.5 |
| $N_2$ used amount [kg/hr] | 3.0 | 3.0 | 1.5 | 3.0 | 0.3 |
| Cooling water used amount [kg/hr] | 2,573 | 2,685 | 2,393 | 3,010 | 3,010 |
| Chiller used amount [kg/hr] | 46.8 | 48.0 | 43.6 | 33.6 | 33.6 |
| Wastewater used amount [kg/hr] | 0.0 | 0.0 | 0.0 | 5.0 | 5.0 |

The steam used amount is a value including an amount at which the steam was used to heat nitrogen. Referring to Table 1, it was confirmed that Comparative Examples 1 and 2 used a large amount of steam as compared to Examples, and used enormous energy to cool the stream recovered after the feed was heated, using a large amount of cooling water and chiller. In addition, it was confirmed that Comparative Examples 1 and 2 had an adverse affect on the environment since the wastewater occurred.

On the contrary, it was confirmed that Examples 1 to 3 could heat the feed even with a small amount of energy and cool the recovered stream. Specifically, the operation cost of Example 1 could be reduced by 53% as compared to that of Comparative Example 1, and could be reduced by 35% as compared to that of Comparative Example 2.

DESCRIPTION OF SYMBOLS 11, 12, 21: Column
13, 15, 22: Condenser

14: Decanter
16, 24: Cooler
23: Drum
110, 210: Mixture including ester-based compound
111: Mixture including ester-based compound from which alcohol is separated
112, 211: Ester-based compound
120: Steam
124: Mixture including alcohol
123, 133: Wastewater
130, 221: Inert gas
220: Fresh inert gas
224: Separated alcohol
132, 225: Separated inert gas
226: Purged inert gas
227: Recovered inert gas

The invention claimed is:

1. A stripping method comprising:
supplying a mixture including a cyclohexane dicarboxylic acid ester-based compound, which is obtained by hydrogenating a phthalate-based compound, to an upper part of a column;
supplying an inert gas to a lower part of the column;
contacting the mixture with an inert gas under a relative pressure of −1.0 to −0.5 barg to remove a volatile component from the mixture, thereby obtaining the cyclohexane dicarboxylic acid ester-based compound; and
supplying the volatile component recovered by contacting the mixture with the inert gas to a synthesis process or a subsequent treatment process of the ester-based compound,
wherein a steam is not supplied to the column.

2. The stripping method of claim 1, wherein:
the mixture includes 1,000 ppm or more of alcohol.

3. The stripping method of claim 1, further comprising:
circulating the inert gas recovered after contacting the mixture with the inert gas, and then contacting the recovered inert gas with a new mixture.

4. The stripping method of claim 1, wherein:
the mixture is contacted with the inert gas at a temperature ranging from 120 to 250° C.

5. The stripping method of claim 4, wherein:
the mixture is heated to 120 to 250° C., the inert gas is heated to 120 to 250° C., and then the heated mixture is contacted with the heated inert gas.

6. The stripping method of claim 1, wherein:
a weight ratio of the mixture and the inert gas is 5 to 30:1.

7. The stripping method of claim 1, wherein:
a volatile component including 500 ppm or less of moisture is recovered as the volatile component.

8. The stripping method of claim 1, wherein:
2-ethylhexanol is recovered as the volatile component.

* * * * *